(12) United States Patent
Froehling et al.

(10) Patent No.: US 6,230,543 B1
(45) Date of Patent: May 15, 2001

(54) HUMIDITY DETECTOR CALIBRATION METHOD

(75) Inventors: Paul H Froehling, Franklin; Gary F Oman, New Berlin; Kurt A Hoefert; George Lewis, both of Milwaukee; Bruce Schultz, West Allis, all of WI (US)

(73) Assignee: Johnson Controls Technology Co., Plymouth, MI (US)

( * ) Notice: Subject to any disclaimer, the term of this patent is extended or adjusted under 35 U.S.C. 154(b) by 0 days.

(21) Appl. No.: 09/422,691

(22) Filed: Oct. 21, 1999

(51) Int. Cl.$^7$ .................................................. G01N 1/00
(52) U.S. Cl. ............................................................ 73/1.06
(58) Field of Search ..................... 73/1.02, 1.06, 73/1.07, 1.88, 335.02–335.05; 361/286; 324/669, 689

(56) References Cited

U.S. PATENT DOCUMENTS

| | | | |
|---|---|---|---|
| 4,800,749 | * 1/1989 | Merrick | 73/1.88 |
| 5,205,151 | * 4/1993 | Shimamura et al. | 73/1.02 |
| 5,408,381 | 4/1995 | Thoma et al. | 361/286 |
| 5,656,928 | * 8/1997 | Suzuki et al. | |
| 5,672,806 | * 9/1997 | Hung | 73/1.06 |

OTHER PUBLICATIONS

Linear Technology, LTC1043 Dual Precision Instrumentation Switched–Capacitor Building Block specification document, Not dated.

* cited by examiner

Primary Examiner—Robert Raevis
(74) Attorney, Agent, or Firm—Quarles & Brady LLP; George E. Haas

(57) ABSTRACT

A humidity detector has a sensor with an electrical characteristic that varies as a function of humidity and a transmitter circuit which produces an output signal in response to the capacitance of the sensor. The humidity detector is calibrated by alternately connecting devices in place of the sensor which simulate performance of the sensor at two reference humidity levels. While each device is present, the transmitter circuit is adjusted so that the output signal indicates the respective reference humidity level. Next, the sensor is connected to the transmitter circuit and exposed to a known humidity level. Then the transmitter circuit is adjusted so that the output signal indicates the known humidity level.

10 Claims, 1 Drawing Sheet

HUMIDITY DETECTOR CALIBRATION METHOD

BACKGROUND OF THE INVENTION

This invention relates to methods for manufacturing electrical humidity detectors, and more particularly to techniques for calibrating such detectors.

Humidity detectors are incorporated into heating, ventilation and air conditioning (HVAC) systems which control the environment within a building. These detectors emit an electrical signal which indicates the level of relative humidity in the zone of the building in which the detector is located. A typical detector comprises a humidity sensor which has a material with an electrical characteristic that varies with variation of humidity to which the sensor is exposed. The sensor is connected to an electrical circuit, often referred to as a transmitter, which normalizes the signal from the sensor and compensates for differences between the actual and ideal electrical characteristics of the sensor.

U.S. Pat. No. 5,408,381 describes one type of a humidity sensor. In this sensor, conductive layers are bounded to opposite faces of a film core. The core is made of a polyimide that has a dielectric constant that varies in a substantially linear manner with humidity. Thus, the capacitance of the sensor changes with the ambient humidity. Because of variations in the polyimide core and manufacturing tolerances, the specific relationship of the capacitance to humidity differs from sensor to sensor and typically differs from the ideal relationship characteristic.

As a consequence of the difference between the actual sensor capacitance and the ideal capacitance, the transmitter circuit to which the sensor is connected provides a mechanism for altering the electrical signal representing humidity in order to compensate for such differences. Conventional transmitters are manufactured with two signal adjustments, offset and gain (or sensitivity). If the output signal from the transmitter is not a linear function of the humidity, a third adjustment may be provided to make the transfer function fit a desired linear characteristic.

During the manufacture of the humidity detector, the electrical signal characteristics are calibrated to match the desired characteristics over the range of relative humidity (RH) with which the detector is intended to operate (e.g. 10–80%). The calibration is performed by adjusting the settings at two widely separated humidity levels within the intended operating range. The procedure requires that the assembled detector be placed within a test chamber that exposes the sensor to an accurately maintained first humidity level for a long enough period for the performance to stabilize. Once the sensor has stabilized, the electrical signal produced by the detector is compared to the ideal signal level indicative of the first humidity level and the offset of the transmitter circuit is adjusted so that the actual signal level matches the ideal.

The gain of the transmitter circuit then is adjusted at a second known humidity level. Because it may take an hour or two for the sensor to stabilize at each humidity level, the detector calibration process is relatively time consuming.

SUMMARY OF THE INVENTION

A humidity detector has a sensor with an electrical characteristic that varies as a function of relative humidity to which the sensor is exposed, and has a transmitter circuit to which the sensor is connected, wherein the transmitter circuit produces an output signal in response to the electrical characteristic of the sensor. The present invention provides a method for calibrating a humidity detector which requires that the sensor be exposed to only a single reference humidity level. This method is predicated on the sensor property that there is a mathematical model of an ideal sensor such that the variability existing in real sensors is related to the model by a constant which multiplies the mathematical model.

That method includes connecting a first reference device to the transmitter circuit in place of the sensor. That first reference device simulates the performance of a model sensor at a first relative humidity level. Preferably the first relative humidity level is chosen to represent a specific value at which the signal offset of the circuit can be adjusted independently of the signal gain. Specifically, the first reference device has an electrical characteristic value which corresponds to the electrical characteristic of the model sensor at the first relative humidity level. The transmitter circuit is adjusted so that the output signal indicates the first relative humidity level. Thereafter, the first reference device is disconnected from the transmitter circuit.

A second reference device then is connected to the transmitter circuit in place of the sensor to simulate performance of the model sensor at a second relative humidity level. Selection of the second relative humidity level is not critical, but preferably should be widely separated from the first relative humidity level. The second reference device has an electrical characteristic value which corresponds to the electrical characteristic of the model sensor at the second relative humidity level. The transmitter circuit is adjusted so that the output signal indicates the second relative humidity level. Thereafter, the second reference device is disconnected from the transmitter circuit.

The sensor then is connected to the transmitter circuit and exposed to a known level of relative humidity. The transmitter circuit is readjusted so that the output signal indicates the known level of relative humidity.

The values of the electrical characteristic for the first and second reference devices can be determined empirically by measuring the performance of a plurality of sensors at the first and second relative humidity levels and then averaging the measurements for each level. Alternatively, a mathematical. model of the relationship between humidity and the electrical characteristic of the sensor can be employed to derive the values of the electrical characteristic for the first and second reference devices.

DETAILED DESCRIPTION OF THE INVENTION

Figure 1:
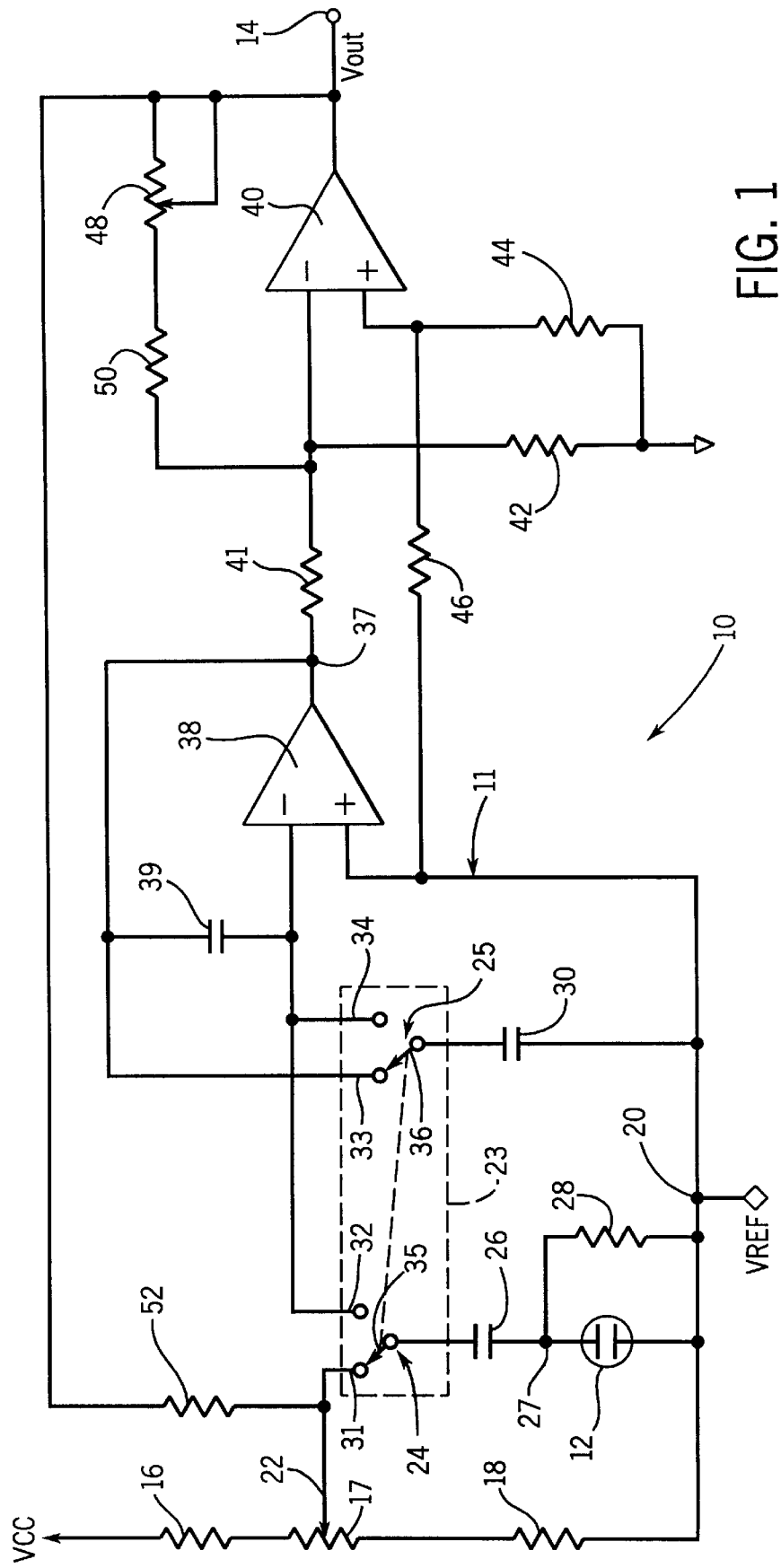
FIG. 1 is a schematic diagram of a humidity detector capable of being calibrated by the present inventive method.

With reference to FIG. 1, a humidity detector 10 incorporates a humidity sensor 12 such as one of the type described in U.S. Pat. No. 5,408,381 which description is incorporated herein by reference. The sensor 12 has a capacitance that varies as a function of the ambient humidity. The humidity sensor 12 is connected to a transmitter circuit 11, which responds to variation in the capacitance of the sensor, by producing a voltage signal Vout at output terminal 14 which indicates the relative humidity. The transmitter circuit 11 includes a voltage divider consisting of resistors 16, 17, and 18 connected in series between a source of positive voltage Vcc and a node 20 to which a reference voltage level Vref is applied. For example, the positive voltage Vcc may be 10.0 volts and the reference voltage level Vref is 2.5 volts.

Resistor 17 is a first potentiometer which acts as an offset adjustment of the transmitter circuit 11 and has a wiper 22 that is connected to one input of a switching circuit 23. The switching circuit 23 preferably is an integrated circuit, such as a model LTC1043 Dual Precision Instrumentation Switched-Capacitor Building Block manufactured by Linear Technology Corporation of Milpitas, Calif., U.S.A. This integrated circuit 23 may be represented schematically as a pair of single-pole, double-throw switches 24 and 25 which are controlled simultaneously by an internal clock having an adjustable frequency. In this particular application, the clock is adjusted to operate the pair of switches 24 and 25 at approximately 8 kHz.

Specifically, the wiper 22 of potentiometer 17 is connected to a first stationary contact 31 of the first switch 24. The common contact 35 of the first switch 24 is coupled to an intermediate node 27 by a first capacitor 26 and the humidity sensor 12 is connected between the intermediate node 27 and the reference voltage node 20. A fixed resistor 28 is connected in parallel with the humidity sensor 12.

A reference capacitor 30 couples the common contact 36 of the second switch 25 to the reference voltage node 20.

The second stationary contacts 32 and 34 of both the first and second switches 24 and 25 are connected to the inverting input of a first operational amplifier 38 which has a non-inverting input connected directly to the reference voltage node 20. An output terminal 37 of the first operational amplifier 38 is connected directly to the first stationary contact 33 of the second switch 25. A charge accumulation capacitor 39 also couples the output terminal 37 to the inverting input of the first operational amplifier 38.

A resistor 41 connects the first operational amplifier's output terminal 37 to the inverting input of a second operational amplifier 40 which input also is coupled to circuit ground by a resistor 42. The non-inverting input of the second operational amplifier 40 is connected to circuit ground by a resistor 44 and to the reference voltage node 20 by another resistor 46. The output of the second operational amplifier 40 produces the output signal Vout of the humidity detector 10 at terminal 14. The output of the second operational amplifier 40 also is connected to its inverting input by the series connection of a second potentiometer 48 and a fixed resistor 50. As will be described, the second potentiometer 48 provides a gain adjustment for the transmitter circuit 11. The output of the second operational amplifier 40 also is coupled by another resistor 52 to the first stationary contact 31 of the first switch 24.

When power is applied to the humidity detector 10, the switching circuit 23 alternately connects the sensor 12 and the reference capacitor 30 to charging voltage sources and to the charge accumulation capacitor 39. When the integrated switching circuit 23 places switches 24 and 25 in the illustrated position where the common contacts 35 and 36 engage the respective first stationary contact 31 and 33, the humidity sensor 12 charges due to the voltage source provided by the voltage divider formed by resistors 16, 17, and 18. While this occurs, the reference capacitor 30 also is being charged to the level of voltage across the charge accumulation capacitor 39.

When the switching circuit 23 changes the position of switches 24 and 25, the associated common contacts 35 and 36 respectively engage the second stationary contacts 32 and 34 (the opposite position to that illustrated in FIG. 1). In this state, the charges on the humidity sensor 12 and the reference capacitor 30 are applied to the inverting input of the first operational amplifier 38. Actually some of the voltage stored across the sensor 12 is utilized to discharge the reference capacitor 30. After that occurs, any voltage remaining across the humidity sensor 12 is applied to the charge accumulation capacitor 39.

The oscillation of switches 24 and 25 continues at the 8 kHz rate and the charge on the charge accumulation capacitor 39 increases as the reference capacitor 30 becomes charged to a level which equals that to which the sensor capacitor 12 charges. That is, the humidity sensor capacitance and the reference capacitance charge to the same level during the charging portion of the switching cycle. At that time, the output voltage from the first operational amplifier 38 becomes stable and no longer fluctuates, as long as the ambient relative humidity to which the humidity sensor 12 is exposed remains constant.

The voltage produced at output terminal 37 by the first operational amplifier 38 is amplified by the second operational amplifier 40 to produce the output voltage level from the detector 10 at terminal 14. This output voltage corresponds to the level of relative humidity observed by the sensor 12.

A change in the relative humidity to which the sensor 12 is exposed, alters its capacitance and thus the charge which accumulates during the charging portion of the switching cycle. This produces a corresponding change in the voltage level across the charge accumulation capacitor 39 and thus the output voltages of the first and second operational amplifiers 38 and 40.

The response of the detector circuit 10 to humidity can be adjusted to conform as substantially as possible to an ideal response characteristic. This is accomplished by adjusting potentiometers 17 and 48. The first potentiometer 17 provides an offset adjustment and the second potentiometer 48 enables the gain of the transmitter circuit 11 to be varied. These potentiometers 17 and 48 are adjusted during a calibration phase of the manufacturing process.

The calibration procedure commences after the transmitter circuitry 11 has been assembled, but before the humidity sensor 12 is connected to that circuitry. Initially, the gain and offset of the transmitter circuit are adjusted while a pair of fixed capacitors are alternately connected in place of the humidity sensor 12. The two fixed capacitors represent the capacitances of an ideal sensor at two different reference humidity levels, for example at 10% and 80% relative humidity.

The values of these fixed capacitors are determined empirically by accurately measuring the capacitance of a number of humidity sensors 12 at the two calibration humidity levels and averaging the capacitance measurements for each level. This produces an average capacitance for each reference humidity level. Obviously, the larger the number of sensors which are measured in this manner, the greater the accuracy that the averages represent performance of the ideal sensor. The fixed capacitors used in the calibration are then selected to match the derived average capacitances as closely as possible.

Alternatively, more sophisticated mathematical modeling of the humidity sensor performance can be performed. In this case, the capacitance of the large number of humidity sensors is measured at numerous points throughout the intended humidity operating range. Those measurements then are employed to develop a polynomial model of the performance of an ideal humidity sensor. The capacitances of the ideal sensor at two widely separated reference humidity levels within that operating range are calculated utilizing the derived model and fixed capacitors having the calculated capacitances are selected.

The first phase of the calibration process is performed by inserting the first fixed capacitor which corresponds to the ideal capacitance at the lower relative humidity level (e.g. 10% RH) into the detector circuit between nodes 20 and 27 in place of the sensor 12. The circuit is then operated and the first potentiometer 17, which sets the offset of the circuit, is adjusted until the output voltage Vout at terminal 14 is at a level which corresponds to that lower relative humidity level.

Then the second fixed capacitor which has a capacitance that corresponds to the capacitance of the humidity sensor 12 at a higher relative humidity level (e.g. 80% RH) is placed in the circuit in place of the first capacitor so as to simulate the sensor 12 at that higher humidity level. The second potentiometer 48 is then adjusted to vary the gain of the transmitter circuit until the output voltage Vout at terminal 14 equals the voltage level which corresponds to that higher humidity level.

During the next phase of the calibration process a real humidity sensor 12 is permanently connected into the circuit. The sensor 12 then is placed into a test chamber and exposed to a constant reference relative humidity which is accurately measured by a highly calibrated instrument. Once the sensor 12 has stabilized at the reference relative humidity of the test chamber, the first potentiometer 17 is adjusted until the output voltage Vout corresponds to the voltage level indicative of the reference relative humidity. The calibration process then is complete.

This calibration process which utilizes fixed capacitors to simulate the performance of an ideal sensor at specific humidity levels, allows the detector 10 to be calibrated by exposing an actual humidity sensor 12 to only one level of known relative humidity. This greatly facilitates and quickens the calibration process.

What is claimed is:

1. A method for calibrating a humidity detector which includes a sensor having an electrical characteristic that varies as a function of humidity to which the sensor is exposed and which includes a transmitter circuit to which the sensor is connected, wherein the transmitter circuit produces an output signal in response to the electrical characteristic of the sensor, said method comprising steps of:
    connecting a first reference device to the transmitter circuit in place of the sensor, wherein the first reference device has a first value of the electrical characteristic which corresponds to performance of the sensor at a first predefined humidity level;
    adjusting the transmitter circuit so that the output signal is indicative of the first predefined humidity level;
    disconnecting the first reference device from the transmitter circuit;
    connecting a second reference device to the transmitter circuit in place of the sensor, wherein the second reference device has a second value of the electrical characteristic which corresponds to performance of the sensor at a second predefined humidity level;
    adjusting the transmitter circuit so that the output signal is indicative of the second predefined humidity level;
    disconnecting the second reference device from the transmitter circuit;
    connecting the sensor to the transmitter circuit;
    exposing the sensor to a known level of humidity;
    adjusting the transmitter circuit so that the output signal is indicative of the known level of humidity.

2. The method as recited in claim 1 wherein the electrical characteristic is capacitance, and the first reference device and the second reference device are capacitors.

3. The method as recited in claim 1 wherein the first value of the electrical characteristic of the first reference device is determined by measuring the electrical characteristic of a plurality of sensors upon being exposed to the first predefined humidity level; and the second value of the electrical characteristic of the second reference device is determined by measuring the electrical characteristic of a plurality of sensors upon being exposed to the second predefined humidity level.

4. The method as recited in claim 3 wherein the first value of the electrical characteristic is determined by averaging measurements of the electrical characteristic of a plurality of sensors upon being exposed to the first predefined humidity level; and the second value of the electrical characteristic is determined by averaging measurements of the electrical characteristic of a plurality of sensors upon being exposed to the second predefined humidity level.

5. The method as recited in claim 1 wherein the first value of the electrical characteristic of the first reference device and the second value of the electrical characteristic of the second reference device are determined from a mathematical model of the sensor.

6. The method as recited in claim 1 wherein the steps of adjusting the transmitter circuit comprise adjusting offset and gain of the transmitter circuit.

7. A method for calibrating performance of a humidity detector with a sensor having a capacitance that varies as a function of humidity to which the sensor is exposed and with a transmitter circuit to which the sensor is connected, wherein the transmitter circuit produces an output signal in response to the capacitance of the sensor, said method comprising steps of:
    connecting a first reference capacitor to the transmitter circuit in place of the sensor, wherein the first reference capacitor has a first capacitance value which corresponds to a value of the capacitance of the sensor at a first predefined humidity level;
    adjusting the transmitter circuit so that the output signal is indicative of the first predefined humidity level;
    disconnecting the first reference capacitor from the transmitter circuit;
    connecting a second reference capacitor to the transmitter circuit in place of the sensor, wherein the second reference capacitor has a second capacitance which corresponds to a value of the capacitance of the sensor at a second predefined humidity level;
    adjusting the transmitter circuit so that the output signal is indicative of the second predefined humidity level;
    disconnecting the second reference capacitor from the transmitter circuit;
    connecting the sensor to the transmitter circuit;
    exposing the sensor to a known level of humidity;
    adjusting the transmitter circuit so that the output signal is indicative of the known level of humidity.

8. The method as recited in claim 7 wherein the steps of adjusting the transmitter circuit comprise adjusting offset and gain of the transmitter circuit.

9. The method as recited in claim 7 wherein adjusting the transmitter circuit so that the output signal is indicative of the first predefined humidity level comprises adjust a signal offset.

10. The method as recited in claim 7 wherein adjusting the transmitter circuit so that the output signal is indicative of the second predefined humidity level comprises adjust a signal gain.

* * * * *